United States Patent [19]

Ito et al.

[11] Patent Number: 5,167,960
[45] Date of Patent: Dec. 1, 1992

[54] HIRUDIN-COATED BIOCOMPATIBLE SUBSTANCE

[75] Inventors: Ralph K. Ito, Quincy; Frank W. LoGerfo, Belmont, both of Mass.

[73] Assignee: New England Deaconess Hospital Corporation, Boston, Mass.

[21] Appl. No.: 227,700

[22] Filed: Aug. 3, 1988

[51] Int. Cl.$^5$ .................... A61F 2/00; A61K 9/22
[52] U.S. Cl. .................... 424/423; 424/424; 424/425; 424/426; 424/422; 523/112; 523/113; 604/890.1; 604/113; 530/300
[58] Field of Search .................... 424/423–426, 424/443; 523/112, 113; 604/266

[56] References Cited

U.S. PATENT DOCUMENTS

| | | | |
|---|---|---|---|
| 3,432,596 | 3/1969 | Markwrdt et al. | 424/95 |
| 4,116,898 | 9/1978 | Dudley et al. | 523/112 |
| 4,378,803 | 4/1983 | Takagi et al. | 523/112 X |
| 4,447,562 | 5/1984 | Ivani | 523/113 X |
| 4,521,564 | 6/1985 | Solomon et al. | 523/112 X |
| 4,563,485 | 1/1986 | Fox, Jr. et al. | 523/113 |
| 4,594,407 | 6/1986 | Nyilas et al. | 523/113 X |
| 4,600,652 | 7/1986 | Solomon et al. | 523/112 X |
| 4,654,302 | 3/1987 | Fritz et al. | 435/70 |
| 4,668,662 | 5/1987 | Tripier | 514/12 |
| 4,680,177 | 7/1987 | Gray et al. | 424/101 |
| 4,713,446 | 12/1987 | DeVore et al. | 523/113 X |
| 4,720,512 | 1/1988 | Hu et al. | 523/112 |
| 4,734,097 | 3/1988 | Tanabe et al. | 524/557 X |

FOREIGN PATENT DOCUMENTS

| | | |
|---|---|---|
| 168342 | 1/1986 | European Pat. Off. |
| 171024 | 2/1986 | European Pat. Off. |
| 193175 | 9/1986 | European Pat. Off. |
| 0225633 | 9/1986 | European Pat. Off. |
| 207956 | 1/1987 | European Pat. Off. |
| 252854 | 1/1988 | European Pat. Off. |
| 7900638 | 9/1979 | PCT Int'l Appl. |
| 8603517 | 6/1986 | PCT Int'l Appl. |
| 2164343 | 3/1986 | United Kingdom ......... 523/113 |

OTHER PUBLICATIONS

Markwardt, (1970), Methods in Enzymol., 19:924–932.
Bagdy et al., (1976), Methods in Enzymol., 45:669–678.
Lindon et al., (1978), J. Lab. Clin. Med., 91:47–59.
Salzman et al., (1980), J. Clin. Invest., 65:64–73.
Van Obberghen-Schilling et al., (1982), Biochemical and Biophysical Research Communications, 106:79–86.
Hoffman et al., (1984), Haemostatis, 14:164–169.
Lindon et al., (1985), J. Lab. Clin. Med., 105:219–226.
Bizios et al., (1985), Thrombosis Research, 38:425–431.
Kottke-Marchant et al., (1985), pp. 842–848.
Castellot, Jr. et al., (1986), Journal of Cellular Physiology, 127:323–329.
Lane et al., (1986), The Journal of Biological Chemistry, 261:3980–3986.
Claggett et al., (1987), in Hemostatis and Thrombosis, Basic Principles and Clinical Practice, (Celman et al., eds.), J. B. Lippincott Co., Philadelphia, Pa., pp. 1348–1365.
Kriauciunas et al., (1987), Diabetes, 36:163–168.
Markwardt, (1987), Thrombosis Research, Suppl. VII, p. 29.
Krstenansky et al., (1987), FEB Letters, 211:10–16.
Company Profile, (1986), Chemist and Druggist, (Oct. 11), pp. 628–629.
Leeches U.S.A. Ltd., (1987), Medical Leeches, pp. 1–7.
Clark et al., (1987), Newsweek (Feb. 2).

(List continued on next page.)

Primary Examiner—Thurman Page
Assistant Examiner—G. S. Kishore
Attorney, Agent, or Firm—Lahive & Cockfield

[57] ABSTRACT

Disclosed is a biocompatible, thromboresistant substance useful for implantable and extracorporeal devices in contact with the vascular system, and methods for producing the same. The biocompatible, thromboresistant substance comprises a synthetic, biocompatible material, at least one biocompatible base coat layer adhered to at least one surface of the material, and a thrombogenesis inhibitor immobilized on the base coat layer via a component capable of binding the inhibitor. The thrombogenesis inhibitor is hirudin, or an active analog or fragment thereof.

35 Claims, 2 Drawing Sheets

OTHER PUBLICATIONS

Salzman et al., (1987), in *Hemostatis and Thrombosis, Basic Principles and Clinical Practice*, (Colman et al., eds.), J. B. Lippincott Co., Philadelphia, Pa., pp. 1335–1340.

Sawyer, (1988), in "Progress in the Development of Hirudin as an Antithrombotic Agent", Minisymposium, D. Path. and Pharm., Stritch School of Medicine, Loyola University Medical Center, Maywood, Ill.

Fink, (1988), in "Progress in the Development of Hirudin as an Antithrombotic Agent", Minisymposium, D. Path. and Pharm., Stritch School of Medicine, Loyola University Medical Center, Maywood, Ill.

Talbot et al., (1988), in "Progress in the Development of Hirudin as an Antithrombotic Agent", Minisymposium, D. Path. and Pharm., Stritch School of Medicine, Loyola University Medical Center, Maywood, Ill.

Fenton, (1988), in "Progress in the Development of Hirudin as an Antithrombotic Agent", Minisymposium, D. Path. and Pharm., Stritch School of Medicine, Loyola University Medical Center, Maywood, Ill.

Fareed et al., (1988), in "Progress in the Development of Hirudin as an Antithrombotic Agent", Minisymposium, D. Path. and Pharm., Stritch School of Medicine, Loyola University Medical Center, Maywood, Ill.

Walenga et al., (1988), in "Progress in the Development of Hirudin as an Antithrombotic Agent", Minisymposium, D. Path. and Pharm., Stritch School of Medicine, Loyola University Medical Center, Maywood, Ill.

Messmore et al., (1988), in "Progress in the Development of Hirudin as an Antithrombotic Agent", Minisymposium, D. Path. and Pharm., Stritch School of Medicine, Loyola University Medical Center, Maywood, Ill.

H--Val----Val----Tyr----Thr----Asp----Cys----Thr----Glu----Ser----Gly-- 10 (A)
--Gln----Asn----Leu----Cys----Leu----Cys----Glu----Gly----Ser----Asn-- 20
--Val----Cys----Gly----Gln----Gly----Asn----Lys----Cys----Ile----Leu-- 30
--Gly----Ser----Asp----Gly----Glu----Lys----Asn----Gln----Cys----Val-- 40
--Thr----Gly----Glu----Gly----Thr----Pro----Lys----Pro----Gln----Ser-- 50
--His----Asn----Asp----Gly----Asp----Phe----Glu----Glu----Ile----Pro-- 60

$$\overset{SO_3H}{|}$$
----Glu----Glu----Tyr----Leu----Gln----OH--

HIRUDIN-COATED BIOCOMPATIBLE SUBSTANCE

BACKGROUND OF THE INVENTION

The technical field of the present invention is prosthetic vascular materials, and more specifically is biocompatible, thromboresistant substances and methods of their preparation.

Exposure of blood to artificial surfaces usually leads to deposition of a layer of adherent platelets, accompanied by activation of the intrinsic coagulation system, and ultimately to the formation of a thrombus. In fact, significant blood/materials interaction can occur on a single pass through a prosthetic arterial graft. The types of blood proteins initially adsorbed or bound to synthetic surfaces may include proteins involved in contact coagulation. Contact coagulation or the extrinsic pathway of coagulation is a complex pathway of biochemical events that induces fibrin formation, platelet and complement activation, chemotaxis, kinin generation, and activation of fibrinolytic components. In addition, each of these events augments subsequent biochemical pathways often controlled by positive and negative feedback loops. Thus, thrombosis induced by contact with artificial materials is a major obstacle in the development and use of internal prostheses and extracorporeal devices such as artificial vessels and organs, and cardiopulmonary bypass and hemodialysis equipment.

Materials having varying degrees of thromboresistance have been utilized in vascular prostheses with limited success. These materials include corroding (self-cleaning) metals, synthetic polymers such as polydimethyl siloxane, Teflon, acylates and methacrylates such as Dacron, electrets, anionic copolymers, and hydrogels (for a review see Salzman et al. (1987) in *Hemostasis and Thrombosis, Basic Principles and Clinical Practice* (Colman et al., eds.) J. B. Lippincott Co., Phila. Pa., pp. 1335-1347).

To decrease the chances of thrombosis due to extended periods of contact with such artificial materials, patients have been treated with systemically administered anti-coagulant, anti-platelet, and thrombolytic drugs. These include any compound which selectively inhibits thromboxane synthetase without affecting prostacycline synthetase, affects platelet adherence as well as aggregation and release, enhances vascular PGI2 production, and/or inhibits both thrombin- and thromboxane-mediated platelet aggregation. Such compounds include aspirin, sulfinpyrazone, dipyridamole, ticlopidine, and suloctidil. However, treatment with these drugs often elicits unwanted side effects including systemic hemmorhaging and the inability to initiate and complete desired clotting elsewhere in the body.

To improve on the thromboresistance of artificial materials, biologically active molecules having thrombolytic, anticoagulating, thrombogenesis-inhibiting, and/or platelet inhibiting abilities have been linked thereto. For example, heparin has been bound to artificial surfaces to reduce cooagulation by activating various inhibitors of the intrinsic clotting system (Salzman et al. (1987) in *Hemostasis and Thrombosis: Basic Principles and Clinical Practice*. 2nd Ed., (Colman et al., eds.), Lippincott Co., Phila., Pa., pp. 1335-1347). However, heparin enhances platelet responses to stimuli such as ADP or collagen, and promotes two adverse primary blood responses towards synthetic surfaces: platelet adhesion and aggregation. In addition, although surface-bound heparin/antithrombin complex may be passive towards platelets, the wide variety of effects it has on interactions with endothelial cell growth factor, inhibition of smooth muscle proliferation, and activation of lipoprotein lipase raises questions as to what adverse effects it may induce over time.

Anti-platelet agents such as $PGE_1$, $PGI_2$ (experimental use only), cyclic AMP, and aspirin have also been attached to solid polymer surfaces. These agents discourage the release of platelet factors that stimulate adverse healing responses in the vicinity of a vascular graft. They may also reduce platelet-aided thrombus formation by inhibiting platelet adhesion.

The exposure of many artificial surfaces to albumin prior to vascular contact results in reduced reactivity with platelets (NIH Publication No. 85-2185, September, 1985, pp. 19-63). Therefore, albumin has been used to coat extracorporeal surfaces before cardiopulmonary by-pass surgery. However, long-term thermoresistance has not been achieved by this procedure.

Fibrinolytically active streptokinase and urokinase, alone or in combination with heparin have been attached to artificial surfaces by Kusserow et al (Trans. Am. Soc. Artif. Intern. Organs (1971) 17:1). These enzymes reduce excessive fibrin deposition and/or thrombotic occlusions. However, the long term assessment of their ability to confer thromboresistance to a synthetic surface has not been determined.

Surface active agents such as Pluronic F-68 have also been immobilized on artificial surfaces, but do not appear to offer long term blood compatibility (Salyer et al. (1971) *Medical Applications of Plastics*. Biomed. Materials Res. Sym. (Gregor, ed.) No. 1 pp. 105).

Therefore, what is needed are better biocompatible materials which are thromboresistant in the long term and whose active components do not cause detrimental side affects.

An object of the present invention is to provide a synthetic, biocompatible, thromboresistent material useful for implantable and extracorporeal devices in contact with bodily fluids.

Another object is to provide an immobilized thrombogenesis inhibitor which is biologically active, and a method of preparing the same.

Still another object of this invention is to provide a method of inhibiting platelet aggregation, the release of platelet factors, and thrombogenesis at the localized site of the graft or prosthesis-blood interface, thus avoiding the systemic effect of antiplatelet and antithrombosis drugs.

SUMMARY OF THE INVENTION

Materials and methods are disclosed herein for the provision of biocompatible, thromboresistant substances useful as a component of implantable or extracorporeal devices in contact with the blood.

It has been discovered that a synthetic, biocompatible material can be made into a thromboresistant substance by immobilizing to it, by way of a base coat layer, the thrombogenesis inhibitor hirudin, or an active analog or fragment thereof, in such a way that does not compromise its thrombogenesis inhibiting activity.

The term "thrombogenesis inhibitor" is used herein to describe a native, synthetic, or recombinant protein, or fragment thereof having the physical and biochemical characteristics of hirudin.

Synthetic materials contemplated by the instant invention are preferably polymers such as Dacron, nylon, polyurethane, cross-linked collagen, polytetrafluoroethylene, polyglycolic acid, and mixtures thereof, the most preferred polymeric material being Dacron. Other synthetic materials might also be used.

At least one layer of biocompatible material is adhered to at least one surface of the synthetic material. This base coat layer contains a component which is capable of binding the thrombogenesis inhibitor. Examples of such base coat components include proteins, peptides, lipoproteins, glycoproteins, glycosaminoglycans, hydrogels, synthetic polymers, and mixtures thereof. In preferred aspects of the invention, the base coat layer includes a protein component such as serum albumin or fibronectin from, for example, human or bovine sources, or mixtures of these proteins. Other materials might also be used to form the base coat layer.

In accordance with the invention, the thrombogenesis inhibitor is immobilized on the synthetic material via a base coat layer which is adhered to least one surface of the synthetic material. The base coat layer contains a component capable of binding the thrombogenesis inhibitor without compromising the biological activity of the inhibitor.

In exemplary aspects of the invention, the synthetic material is activated prior to having the base coat layer adhered thereto so as to enhances its ability to bind the base coat base layer. For example, in one preferred aspect, the synthetic material is contacted with a solution which makes available at least one chemically active group (e.g., a carboxylic acid group) in the material for binding to a bifunctional cross-linking reagent (e.g., carbodiimide). The material so treated is then put into contact with a solution containing the cross-linking carbodiimide reagent for a time sufficient to allow the chemically active group to bind thereto.

In another embodiment, the synthetic material may be contacted with a solution which removes impurities therein and/or thereon prior to the activation step described above.

The immobilization step may be carried out by initially contacting the thrombogenesis inhibitor with at least one molecule of a bifunctional cross-linking reagent for a time sufficient to allow linking of the reagent to the inhibitor, and then binding the thrombogenesis inhibitor-linked reagent to the base coat. The bound thrombogenesis inhibitor retains its thrombogenesis inhibiting activity when bound to the reagent. The bifunctional cross-linking reagent useful for such an immobilization step may be heterobifunctional (e.g., N-succinimidyl 3-(2-pyridyldithio)propionate (SPDP)), homobifunctional (e.g., ethylene glycolbis (succinimidylsuccinate) (EGS)), or a mixture of both.

The term "bifunctional cross-linking reagent" is defined herein as a molecule having the ability to bind to, and therefore link, two reactive groups on, for example, one molecule or two separate molecules. If the bifunctional cross-linking reagent binds two different types of groups, it is a "heterobifunctional" cross-linking reagent. However, if the bifunctional cross-linking reagent binds only to two similar groups, it is "homobifunctional".

Prior to the binding step, the thrombogenesis-linked reagent may be subjected to chromatographic procedures to remove impurities mixed in with it.

In an alternative aspect of the invention, the base coat adhered to the synthetic material may be linked at the same time to at least one molecule of a bifunctional cross-linking reagent. In this embodiment, the method further includes binding the thrombogenesis inhibitor-linked reagent to the base coat-linked reagent, thereby linking the thrombogenesis inhibitor to the material-adhered base coat layer.

In another aspect of the invention, the base coat-linked reagent is reduced prior to the binding step. Reduction results in the formation of sulhydryl groups from the reagent on the base coat which can react with the inhibitor-linked bifunctional cross-linking reagent via a substitution reaction to form an S-S bond, thereby covalently linking the thrombogenesis inhibitor to the base coat.

In yet another aspect of the invention, the base coat is linked to the thrombogenesis inhibitor before it is linked to the synthetic, biocompatible material.

The invention will next be described in connection with certain illustrated embodiments. However, it should be clear that various modifications, additions, and deletions can be made without departing from the spirit or scope of the invention.

BRIEF DESCRIPTION OF THE DRAWING

The foregoing and other objects of the present invention, the various features thereof, as well as the inventions thereof may be more fully understood from the following description when read together with the accompanying drawings in which.

DESCRIPTION OF THE INVENTION

Figure 1:
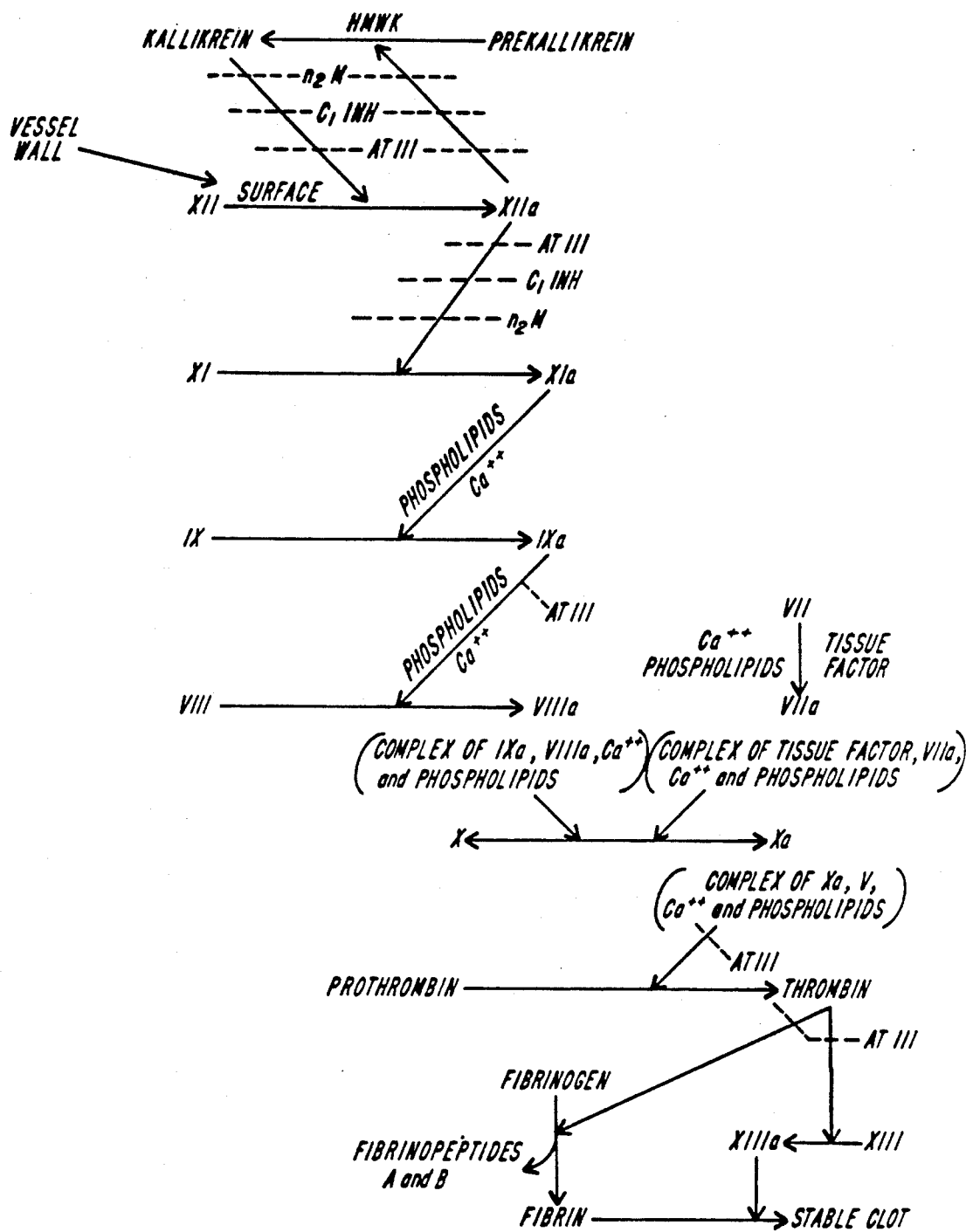
FIG. 1 is a diagrammatic representation of the pathways involved in thrombogenesis.

This invention provides biocompatible, thromboresistant substances useful for implantable and extracorporeal devices in contact with the vascular system, and methods for their fabrication.

The substances provided by this invention include a synthetic biocompatible substance having a thrombogenesis-inhibiting reagent linked thereto via a biocompatible base coat adhered to the material's surface.

The material useful in a prosthetic extracorporeal or implantable device may be composed of any biocompatible, synthetic, preferably polymeric material having enough tensile strength to withstand the rigors of blood circulation, and having groups onto which a base coat can be directly or indirectly bound. Examples of such synthetic materials are polytetrafluoroethylene (Teflon) and Dacron, nylon, and the like. The material may have any dimensions suitable for the purpose for which it is being used. For example, it may be an integral part of an implanted heart valve or of an extracorporeal device used for hemodialysis or cardiopulmonary by-pass surgery, or it may be used to coat catheters or to line the interior of a vascular graft.

The synthetic material, when obtained, may be coated with or contain various noncovalently adhered impurities whose removal may be prerequisite for the adherence of a base coat thereto. For example, lubricants on commercial quality Dacron can be removed by contacting the Dacron with a solution containing, for example, various detergents, solvents, or salts, which loosen and/or solubilize these impurities.

TABLEs 1 and 2 outline representative methods of preparing the biocompatible, thromboresistant substance, where "Da" refers to a synthetic material composed of woven Dacron fibers, and "HSA" refers to human serum albumin.

TABLE 1

| STEP | PROCESS |
|---|---|
| 1) | Da. + NaOH → Da-COOH |
| 2) | Da-COOH + EDC → Da-EDC |
| 3) | Da-EDC + HSA → Da-HSA + urea (EDC by-product) |
| 4) | Da-HSA + SPDP → Da-HSA-SPDP |
| 5) | Da-HSA-SPDP + DTT → Da-HSA-SH + P-2-T |
| 6) | Inhibitor + SPDP → Inhibitor-SPDP |
| 7) | Da-HSA-SH + Inhibitor-SPDP → Da-HSA-S-S-Inhibitor + P-2-T |

TABLE 2

| STEP | PROCESS |
|---|---|
| 1) | HSA + SPDP → HSA-SPDP |
| 2) | HSA-SPDP + DTT → HSA-SH + P-2-T |
| 3) | Inhibitor + SPDP → Inhibitor-SPDP |
| 4) | HSA-SH + Inhibitor-SPDP → HSA-S-S-Inhibitor + P-2-T |
| 5) | Da + NaOH → Da-COOH |
| 6) | Da-COOH + EDC → Da-EDC |
| 7) | Da-EDC + HSA-S-S-Inhibitor → Da-HSA-S S-Inhibitor + urea (EDC by-product) |

Initially, the material may be activated so as to enhance the binding of the base coat layer. This activating step increases the number of chemically active group in the material. For example, alkaline hydrolysis may be performed to increase the number of reactive carboxylic acid groups in the Dacron to which a bifunctional cross-linking reagent such as carbodiimide may be bound. Ultimately, the base coat will adhere to the bound carbodiimide groups on the material. However, this method must be performed with care, as alkaline hydrolysis partially degrades the Dacron, resulting in a fraying of the material's fibers.

At least one base coat layer is adhered to at least one surface of the synthetic material.

This layer, either adhered to the material or unbound, provides components for attachment of the thrombogenesis inhibitor. Such components provide more binding sites for the inhibitor than the synthetic material, alone, thereby amplifying the amount of inhibitor which may be bound. Useful components include proteins, peptides, lipoproteins, glycoproteins, glycosaminoglycans, synthetic polymers, and mixtures thereof. Proteins such as serum albumin and fibronectin are particularly useful for this purpose as they are known to have antithrombogenic properties, themselves, are very desirable as base coat components (Lyman et al. (1965) Trans. Am. Soc. Artif. Intern. Organs 11:301; Falb et al. (1971) Fed. Proc. 30:1688). An HSA molecule, for example, has 65 amino groups available as binding sites.

Attachment of the base coat to the artificial surface may be covalent in nature. Methods to covalently bind proteins to Dacron involve attack of the free reactive succinimide ester group of the cross-linking reagent to primary amino groups on a protein. As shown in the example in TABLE 1, to covalently adhere the base coat to Dacron, the Dacron is initially treated with 0.5 N NaOH and reacted with carbodiimide before it is coated with HSA (base coat) in phosphate buffered saline (PBS).

A thrombogenesis inhibitor useful as a coating for surfaces in contact with blood, bodily fluids, or tissues, is then covalently adhered to the base coat via the component. Inhibitor-coated substances are ideal for implantable use in devices which are in direct contact with blood. For example, by-pass grafts used to replace blood vessels often become filled with blood clots or thrombi, resulting in restricted blood flow. Since the inhibitor-coated substance is resistant to formation of blood clots, thrombosis and subsequent blockage of the bypass graft will be prevented. Likewise when catheters are placed into the vascular system for a diagnostic or therapeutic purposes, a blood clot often forms on the outside of the catheter. The clot may be washed off the catheter by flowing blood, or be jarred loose by manipulation of the catheter, increasing the possibility of embolism and blockage of the circulation to vital organs. Inhibitor-coated substances provide similar advantages for artificial or prosthetic heart valves, intra-aortic balloon pumps, total or artificial heart or heart assist devices, intracaval devices, and any device in contact with the bloodstream. In addition, inhibitor-coated devices provide advantages for intracavity devices such as intraperitoneal dialysis catheters and subcutaneous implants where the thrombogenesis-induced inflammmatory reactions would be diminished.

Thrombogenesis inhibitors useful for these purposes include hirudin and active analogs, fragments, derivatives, and fusion products thereof, or mixtures thereof.

Figures 2, 3:
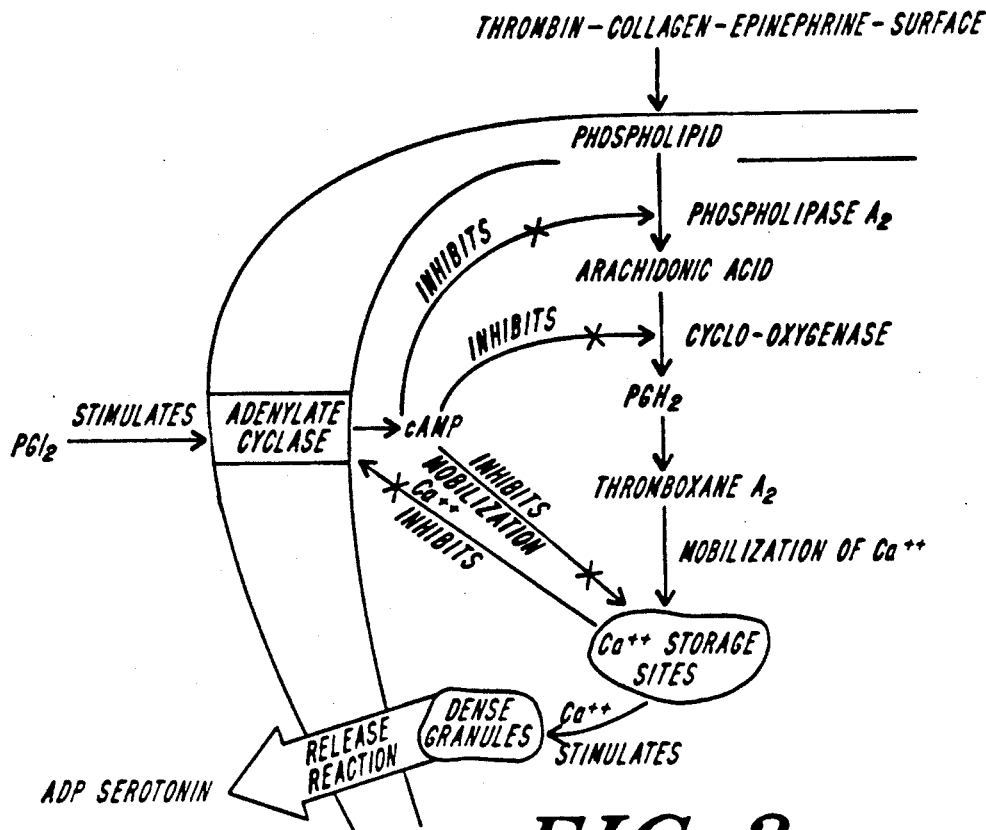
FIG. 2 is a diagrammatic representation of platelet involvement in thrombogenesis.
FIG. 3 is a schematic representation of the amino acid sequence of native hirudin.

Hirudin is a protein isolated from the saliva of leeches, the amino acid sequence of which is shown in FIG. 3. Hirudin has been shown to reduce platelet adhesiveness, a characteristic which is probably attributed to its mode of action on thrombin. This property alone makes hirudin a most attractive anticoagulant when synthetic surfaces interface with blood. It also selectively inhibits the ability of thrombin to be proteolytic, to be mitogenic for fibroblasts, to activate platelets, and to have chemotatic properties for monocytes and polymorphonuclear leukocytes. In addition, the immobilized hirudin-thrombin complex may down-regulate the events of thrombin mediated chemotaxis. This is a significant event as chronic inflammation may be due to the release by polymorphonuclear leukocytes of degradative enzymes and superoxides throughout the graft that show effects at the sites of the anastomosis, contributing to anastomotic hyperplasia.

A number of synthetic and recombinant hirudin analogs exist (e.g., CGP39393 produced by recombinant DNA techniques by Ciba-Geigy, Basel, Switzerland; PCT W079/00638; PCT W086/03517) which are at least equally useful as thrombogenesis inhibitors.

The thrombogenesis inhibitor is directly or indirectly immobilized on the base coat via the use of a bifunctional cross-linking reagent. In particular, a heterobifunctional cross-linking reagent which has two different reactive groups at each end of a linear molecule, and can therefore bind two different reactive groups on other molecules or on a different region of the same molecule, is most useful as a bifunctional cross-linking agent. For example, photoreactive cross-linkers, such as sulfosuccinimidyl 2-(m-azodo-o-nitro-benzamido)-ethyl-1, 3'-dithio-propionate (SAND), or N-succinimidyl-6-(4-azoido-2'-nitrophenyl-amino) hexanoate (SANPAH) have a photoreactive group that can directly insert into C-H bonds of the base coat by photochemical coupling, while the other group remains free to bind to proteins.

Other useful and preferable cross-linking reagents (such as SPDP) and their characteristics are found in TABLE 3. In TABLE 3, the "Double-Agent Number" listed for each reagent is the commercial designation for the reagent as made available by Pierce Chemical Co. (Rockford, Ill.).

TABLE 3

CROSS-LINKING REAGENTS

| Double-Agent Number | Double-Agent Acronym | Bifunctionality Homo | Bifunctionality Hetero | Reactive towards: $NH_2$ | Reactive towards: SH | Photo-Reactive |
|---|---|---|---|---|---|---|
| 21551 | ANB-NOS | | X | X | | X |
| 20106 | APB | | X | | X | X |
| 20107 | APG | | X | X | | X |
| 21559 | APTP | | X | | X | X |
| 21579 | BS³ | X | | X | | |
| 22319 | BMH | X | | | X | |
| 21554 | BSOCOES | X | | X | | |
| 21524 | DFDNB | X | | X | | |
| 20047 | DIDS | X | | X | | |
| 20664 | DMA | X | | X | | |
| 20666 | DMP | X | | X | | |
| 20668 | DMS | X | | X | | |
| 22585 | DSP | X | | X | | |
| 21555 | DSS | X | | X | | |
| 20590 | DST | X | | X | | |
| 20665 | DTBP | X | | X | | |
| 22590 | DTBPA | X | | . | | X |
| 21577 | DTSSP | X | | X | | |
| 21550 | EADB | | X | | | X |
| 21565 | EGS | X | | X | | |
| 23700 | FNPA | | X | X | | X |
| 21560 | HSAB | | X | X | | X |
| 26095 | MABI | | X | X | | X |
| 22310 | MBS | | X | X | X | |
| 27715 | NHS-ASA | | X | X | | X |
| 20669 | PNP-DTP | | X | X | | X |
| 21552 | SADP | | X | X | | X |
| 21549 | SAND | | X | X | | X |
| 22588 | SANPAH | | X | X | | X |
| 27716 | SASD | | X | X | | X |
| 22325 | SIAB | | X | X | X | X |
| 22320 | SMCC | | X | X | X | |
| 22315 | SMPB | | X | X | X | |
| 21557 | SPDP | | X | X | X | |
| 21556 | Sulfo-BSOCOES | X | | X | | |
| 20591 | Sulfo-DST | X | | X | | |
| 21556 | Sulfo-EGS | X | | X | | |
| 22312 | Sulfo-MBS | | X | X | X | |
| 21553 | Sulfo-SADP | | X | X | | X |
| 22589 | Sulfo-SANPAH | | X | X | | X |
| 22327 | Sulfo-SIAB | | X | X | X | |
| 22322 | Sulfo-SMCC | | X | X | X | |
| 22317 | Sulfo-SMPB | | X | X | X | |
| 26101 | TRAUT'S | X | | X | | |

CROSS-LINKING REAGENTS (part B)

| Agent Acronym | Chemical Name |
|---|---|
| ANB-NOS | N-5-azido-2-nitrobenzoyloxysuccinimide |
| APB | p-azidophenacyl bromide |
| APG | p-azidophenyl glyoxal |
| APTP | n-4-(azidophenylthio)phthalimide |
| BS³ | bis(sulfosuccinimidyl) suberate |
| BMH | bis maleimidohexane |
| BSOCOES | bis[2-(succinimidooxycarbonyloxy)ethyl]sulfone |
| DFDNB | 1,5-difluoro-2,4-dinitrobenzene |
| DIDS | 4,4'-diisothiocyano-2,2'-disulfonic acid stilbene |
| DMA | dimethyl adipimidate-2 HCl |
| DMP | dimethyl pimelimidate-2 HCl |
| DMS | dimethyl suberimidate-2 HCl |
| DSP | dithiobis(succinimidylpropionate) |
| DSS | disuccinimidyl suberate |
| DST | disuccinimidyl tartarate |
| DTBP | dimethyl 3,3'-dithiobispropionimidate-2-HCl |
| DTBPA | 4,4'-diothiobisphenylazide |
| DTSSP | 3,3-dithiobis(sulfosuccinimidyl-propionate) |
| EADB | ethyl-4-azidophenyl 1,4-dithio-butyrimidate |
| EGS | ethylene glycolbis(succinimidyl-succinate) |
| FNPA | 1-azido-4-fluoro-3-nitobenzene |
| HSAB | N-hydroxysuccinimidyl-4-azidobenzoate |
| MABI | methyl-4-azidobenzoimidate |
| MBS | m-maleimidobenzoyl-N-hydroxysulfo-succinimide ester |
| NHS-ASA | N-hydroxysuccinimidyl-4-azidosalicylic acid |
| PNP-DTP | p-nitrophenyl-2-diazo-3,3,3-trifluoro-propionate |
| SADP | N-succinimidyl(4-axidophenyl)-1,3'-dithiopropionate |
| SAND | sulfosuccinimidyl 2-(m-azido-o-nitro-benzamido)-ethyl-1,3'-dithiopropionate |
| SANPAH | N-succinimidyl-6(4'-azido-2'-nitrophenyl-amino)hexanoate |
| SASD | sulfosuccinimidyl 2-(p-azidosalicyl-amido)ethyl-1,3'-dithio-propionate |
| SIAB | N-succinimidyl(4-iodoacetyl)amino-benzoate |
| SMCC | succinimidyl 4-(N-maleimidomethyl)-cyclohexane-1-carboxylate |
| SMPB | succinimidyl 4-(p-maleimidophenyl)-butyrate |
| SPDP | N-succinimidyl 3-(2-pyridyldithio)propionate |
| Sulfo-BSOCOES | bis[2-(sulfosuccinimidooxy-carbonyloxy)ethyl]sulfone |
| Sulfo-DST | disulfosuccinimidyl tartarate |
| Sulfo-EGS | ethylene glycolbis(sulfosuccinimidyl-succinate) |
| Sulfo-MBS | m-maleimidobenzoyl-N-hydro-xysulfo-succinimide ester |
| Sulfo-SADP | sulfosuccinimidyl(4-azidophenyldithio)-propionate |
| Sulfo-SANPAH | sulfosuccinimidyl 6-(4'azido-2'-nitro-phenylamino)hexanoate |
| Sulfo-SIAB | sulfosuccinimidyl(4-iodoacetyl)amino-benzoate |
| Sulfo-SMCC | sulfosuccinimidyl 4-(N-maleimido-methyl)cyclohexane-1-carboxylate |
| Sulfo-SMPB | sulfosuccinimidyl 4-(p-maleimido-phenyl)butyrate |
| TRAUT'S | 2-iminothiolane-HCl |

The cross-linking reagent is applied to the base coat in amounts such that the desired binding site density is achieved. Binding site density is that amount of cross-linking reagent, in terms of moles/g synthetic material, to bind to the base coat while providing confluent coverage of the surface.

To put the inhibitor in condition for linkage to the base coat, the cross-linking reagent may be initially coupled separately to both the base coat and to the inhibitor. The kinetic constants of the inhibitors are compared before and after coupling to evaluate effects of the procedure on their kinetic constants. The inhibitor should remain biologically active after being coupled. Therefore, standard activity assays specific for the inhibitor to be immobilized are performed using a standard thrombin solution to evaluate this capacity.

As an alternative, the protein component of the base coat may be bound to the thrombogenesis inhibitor forming a conjugate prior to its adherence to the synthetic material, and the conjugate bound to the synthetic material as shown in TABLE 2. In addition, thrombogenesis inhibitor conjugate retains biological activity, and can be used as an agent to increase the half life in the circulation as it is not easily cleared by the kidney.

In the special case of SPDP derivatization of hirudin, linkage of certain groups on hirudin to SPDP may destroy hirudin's biological activity because at least some of these groups are required for activity. However, by adjusting the reaction ratio of hirudin to SPDP (1:4, mole:mole), and running the reaction at near physiological pH, SPDP becomes somewhat selective for epsilon amino groups. The result of these conditions favor a 1:1 (mole:mole) conjugation ratio of hirudin to SPDP covalently bound without destroying hirudin's biological activity.

SPDP will react with terminal as well as epsilon amino groups, Since derivatization of a terminal amino group can inactivate a biologically active protein, T-BLOCK (Pierce Chemical Co., Rockford, Ill.) may be used to block that group during SPDP-derivatization. The T-BLOCK is then removed after derivatization to restore biological activity.

The invention will be further understood from the following, non-limiting examples.

EXAMPLE 1

A. Pretreatment and Activation of Dacron

Dacron polyester 52 (DuPont) is sectioned into 1.0 cm lengths. The lubricant on and in the woven surface is removed by washing once for 1 hr with carbon tetrachloride, and twice with 100% $CH_3OH$. The methanol is removed by multiple water washes, followed by one wash in phosphate buffered saline (PBS), pH 7.4.

The graft material is then subjected to alkaline hydrolysis to increase available COOH groups. The material is treated with 0.5 M NaOH at 50° C. for 1 hr. It is then washed with $H_2O$ repeatedly, and the following steps initiated immediately.

B. Carbodiimide Derivatization of Activated Dacron

The activated material is placed into 100.0 ml of 10 mM water-soluble carbodiimide (EDC) in deionized water, pH 4.6–5.0, for 1 hour at RT with constant stirring. The material is removed and washed in PBS to remove excess unbound EDC.

C. Base Coat Formation

The base coat is applied to the lumen of the Dacron graft material The derivatized Dacron material is incubated in a 5% HSA solution in PBS at 1 ml/cm² graft material for 24 hr at RT with constant stirring. The graft is removed and washed in PBS to remove nonspecifically bound HSA. Approximately 20 mg protein/mg Dacron is covalently bound.

D. Linkage of SPDP to the Base Coat

The HSA-bound Dacron material is incubated in a 1.0 mM solution of SPDP in PBS, pH 7.4, to bind SPDP to the HSA (100 mM SPDP/cm² base coat). Incubation is terminated after 30–40 min at RT. The graft is washed in PBS to remove nonspecifically bound SPDP.

E. Activation of SPDP on Base Coat and Measurement of Binding Site Density

The SPDP-linked material is dried and weighed to obtain its absolute weight It is then placed in a 50 mM solution of dithiotreitol (DTT) for 5 min at RT. This reaction releases pyridine-2-thione (P-2-T) from the bound SPDP, and simultaneously forms free sulphydryl (SH) groups on the base coat. The released P-2-T is quantitated by absorption spectrophotometry at 343 nm using its extinction coefficient ($E = 8.08 \times 10^3$), and is directly proportional to the quantity of bound SPDP or binding sites. The number of binding sites are calculated and expressed as moles of sites/g of Dacron.

The material is then washed 5 times in PBS and 4 times in $dH_2O$.

F. Linkage of SPDP to Hirudin

Lyophillized hirudin is resuspended in PBS at 1 mg/ml. SPDP (Pharmacia, Piscataway, N.J.) is dissolved in 100% ETOH to 10 mM. One part hirudin is mixed with 4 parts SPDP (mole:mole), and incubated for 30 min at RT. SPDP-bound-hirudin is then separated from free SPDP and reaction by-products by chromatography on a G-25 column; the derivatized hirudin is eluted first.

G. Measurement of SPDP Bound to Hirudin

The binding of SPDP to hirudin can be quantitated by the addition of DTT which liberates pyridine-2-thione (P-2-T) from SPDP bound to hirudin, and which can be measured spectrophotometrically at 343 nm. From this measurement, the moles of SPDP bound to hirudin can be calculated. Each P-2-T released represents one covalent attachment of SPDP to hirudin. One mole of hirudin binds per 1.2 moles SPDP in the present studies.

H. Linkage of Derivatized Hirudin to Base Coat

The reduced SPDP-linked base coat (having free SH groups) is washed with PBS to remove the DTT. SPDP-linked hirudin is then added to the graft at 50.0 mg/cm² Dacron. The solution is incubated overnight at RT to allow the binding of SPDP-hirudin to SH groups on the Dacron graft. The Dacron material with hirudin covalently immobilized thereto is then washed and stored in PBS.

I. Analysis

A. Spectrophotometric Assays:

To quantitate the amount of SPDP-hirudin immobilized on the base coat, an absorbance reading is taken at 343 nm of the solution at the time of the addition of SPDP-hirudin to the Dacron. After the overnight incubation period, another absorbance reading is taken, and the change in absorbance is due to the quantity of P-2-T released from SPDP-hirudin. The amount of P-2-T released is directly proportional to the number of SPDP substitution reactions that have occurred between the base coat SH groups and SPDP-hirudin.

B. Thrombin Inhibition Assay:

Using a known amount of thrombin, a standard curve is constructed with known amount of hirudin or hirudin analog by adding hirudin to thrombin, and measuring residual thrombin activity using chromatographic substrate S-2238. Thrombin inhibition by derivatized hirudin (hirudin-SPDP) or immobilized hirudin (the Dacron material with immobilized hirudin) is then compared to nonderivatized hirudin values by equating ED50 values using 10 NIH units/ml thrombin, and measuring residual thrombin activity.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. A biocompatible, thromboresistent substance comprising:
   (a) a synthetic, polymeric, biocompatible material;
   (b) at least one biocompatible base coat layer adhered to at least one surface of said material; and
   (c) a thrombogenesis inhibitor immobilized on said base coat layer, said inhibitor being hirudin or an active analog or active fragment thereof,
   said base coat layer having a component capable of binding said thrombogenesis inhibitor.

2. The substance of claim 1 wherein said polymer is selected from the group consisting of polyethylene terphthalate, nylon, polyurathane, cross-linked collagen, polyglycolic acid, polytetrafluoroethylene, and mixtures thereof.

3. The substance of claim 2 wherein said polymer comprises polyethylene terphthalate.

4. The substance of claim 1 wherein said base coat layer comprises a component selected from the group consisting of a protein, peptide, lipoprotein, glycoprotein, glycosaminoglycan, hydrogel, synthetic polymer, and mixtures thereof.

5. The substance of claim 4 wherein said component of said base coat layer comprises a protein.

6. The substance of claim 5 wherein said protein is selected from the group consisting of serum albumin, fibronectin, and mixtures thereof.

7. The substance of claim 6 wherein said protein comprises bovine serum albumin.

8. The substance of claim 6 wherein said protein comprises human serum albumin.

9. The substance of claim 6 said protein comprises bovine fibronectin.

10. The substance of claim 6 wherein said protein comprises human fibronectin.

11. The substance of claim 1 further comprising a bifunctional cross-linking reagent linking said thrombogenesis inhibitor to said base coat layer.

12. The substance of claim 11 wherein said bifunctional cross-linking reagent is heterobifunctional.

13. The substance of claim 11 wherein said bifunctional cross-linking reagent is homobifunctional.

14. The substance of claim 12 wherein said heterobifunctinoal cross-linking reagent comprises SPDP.

15. A method of producing a biocompatible, thromboresistant substance, said method comprising the steps of:
   (a) adhering at least one base coat layer to at least one surface of a synthetic, polymeric, biocompatible material, said base coat layer containing a component capable of binding a thrombogenesis inhibitor; and
   (b) immobilizing said thrombogenesis inhibitor to said base coat layer, said inhibitor being hirudin or an active analog or active fragment thereof.

16. The method of claim 15 wherein said adhering step comprises:
   (a) activating said material so as to enhance the binding of said base coat layer thereto; and
   (b) contacting said activated material with said base coat layer for a time sufficient to allow said component of said base coat layer to bind to said activated material.

17. The method of claim 15 wherein said adhering step comprises adhering a base coat layer to at least one surface of said material, said base coat layer containing a component selected from the group consisting of a protein, peptide, lipoprotein, glycoprotein, hydrogel, glycosaminoglycan, synthetic polymer, and mixtures thereof.

18. The method of claim 17 wherein said adhering step further comprises adhering a base coat layer containing a protein to at least one surface of said material.

19. The method of claim 18 wherein said adhering step further comprises adhering a base coat layer to at least one surface of said material, said base coat layer containing a protein selected from the group consisting of serum albumin, fibronectin, and mixtures thereof.

20. The method of claim 19 wherein said adhering step further comprises adhering a base coat layer containing human serum albumin to at least one surface of said material.

21. The method of claim 19 wherein said adhering further comprises adhering a base coat layer containing bovine serum albumin to at least one surface of said material.

22. The method of claim 19 wherein said adhering step further comprises adhering a base coat layer containing human fibronectin to at least one surface of said material.

23. The method of claim 19 wherein said adhering step further comprises adhering a base coat layer containing bovine fibronectin to at least one surface of said material.

24. The method of claim 16 wherein said activating step comprises the steps of:
   (a) treating said material with a solution that makes available for binding at least one chemically reactive group in said material; and
   (b) contacting said treated material with a solution containing a bifunctional cross-linking reagent for a time sufficient to allow binding of said chemically reactive group to said reagent.

25. The method of claim 24 wherein said treating step further comprises treating said material with a solution that makes available for binding at least one chemically active group in said material, said chemically active group being a carboxylic acid group.

26. The method of claim 15 further comprising the preliminary step of contacting said material with a solution which removes impurities thereon, said preliminary step being performed prior to said adhering step.

27. The method of claim 15 wherein said mobilizing step further comprises the steps of:
   (a) contacting said thrombogenesis inhibitor with a at least one molecule of a bifunctional cross-linking reagent for a time sufficient to allow linking of said reagent to said thrombogenesis inhibitor; and
   (b) binding said thrombogenesis inhibitor-linked reagent to said base coat, said linked thrombogenesis inhibitor having thrombogenesis inhibiting activity.

28. The method of claim 27 wherein said contacting step further comprises contacting said base coat with at least one molecule of said bifunctional cross-linking reagent for a time sufficient to allow linking of said agent to said base coat, and said binding step further includes binding said thrombogenesis inhibitor-linked reagent to said base coat-linked reagent.

29. The method of claim 27 wherein said contacting step further includes contacting said thrombogenesis inhibitor with at least one molecule of said bifunctional cross-linking reagent selected from the group consisting of heterobifunctional cross-linking reagents, homobifunctional cross-linking reagents, and mixtures thereof.

30. The method of claim 28 wherein said contacting step includes contacting said base coat with at least one molecule of said bifunctional cross-linking reagent selected from the group consisting of heterobifunctional cross-linking reagents, homobifunctional cross-linking reagents, and mixtures thereof.

31. The method of claim 30 further comprising the steps of:
(a) reducing said base coat-linked reagent to expose a sulfhydryl group thereon;
(b) adding said inhibitor-linked reagent to the exposed sulfhydryl group thereon; and
(c) inducing a substitution reaction involving said sulfhydryl group and said inhibitor-linked reagent, said reaction resulting in linkage of said base coat to said inhibitor.

32. The method of claim 29 wherein said contacting step includes contacting said thrombogenesis inhibitor with the heterobifunctional cross-linking reagent, N-succinimidyl 3-(2-pyridylaithio)propionate (SPDP).

33. The method of claim 30 wherein said contacting step includes contacting said thrombogenesis inhibitor with the heterobifunctional crosslinking reagent, SPDP.

34. The method of claim 27 further comprising the additional step of subjecting said thromogenesis-linked reagent to a chromatographic procedure to remove impurities therein, said additional step being performed after said contacting step and prior to said binding step.

35. A method of producing a biocompatible, thromboresistant substance, said method comprising the steps of:
(a) immobilizing a thrombogenesis inhibitor to a base coat layer,
said inhibitor being hirudin or an active analog or active fragment thereof, and
said base coat layer containing a component capable of binding said thrombogenesis inhibitor; and
(b) adhering said base coat layer linked to said thromogenesis inhibitor to at lest one surface of a synthetic, polymeric, biocompatible material.

* * * * *